United States Patent [19]

Klinkhammer

[11] Patent Number: 5,497,526
[45] Date of Patent: Mar. 12, 1996

[54] TOOTH BRUSHING DEVICE

[75] Inventor: Ronald W. Klinkhammer, Seattle, Wash.

[73] Assignee: Oral Logic Inc., Minot, N. Dak.

[21] Appl. No.: 363,965

[22] Filed: Dec. 23, 1994

Related U.S. Application Data

[63] Continuation of Ser. No. 238,144, May 4, 1994, abandoned, which is a continuation of Ser. No. 975,013, Nov. 12, 1993, abandoned, which is a division of Ser. No. 499,022, Mar. 26, 1990, Pat. No. 5,171,066, which is a continuation-in-part of Ser. No. 145,771, Jan. 19, 1988, abandoned, which is a continuation-in-part of Ser. No. 937,554, Dec. 4, 1986.

[51] Int. Cl.$^6$ ........................................................ A46B 9/04
[52] U.S. Cl. ........................... 15/167.2; 15/176.1; 15/187; 15/201; 15/207.2; 132/309
[58] Field of Search ....................... 15/167.1, 167.2, 15/172, 176.1, 176.6, 186–188, 201–203, 207.2; 132/308, 309; 601/141

[56] References Cited

U.S. PATENT DOCUMENTS

| | | | |
|---|---|---|---|
| 1,225,955 | 5/1917 | Hickman | 15/167.2 |
| 1,616,484 | 2/1927 | Beynon | 15/167.2 |
| 1,668,216 | 5/1928 | Noel | 15/201 |
| 1,709,262 | 4/1929 | Henderhan | 15/167.2 |
| 1,894,509 | 1/1933 | Booth | 15/201 |
| 2,284,200 | 5/1942 | Gruss | 15/188 |
| 2,807,820 | 10/1957 | Dinhofer | 15/176.1 |
| 3,707,013 | 12/1972 | Erkers | 15/187 |
| 4,423,531 | 1/1984 | Wall | 15/201 |
| 4,972,542 | 11/1990 | Moshos et al. | 15/176.6 |

FOREIGN PATENT DOCUMENTS

| | | | |
|---|---|---|---|
| 452708 | 3/1913 | France | 15/201 |
| 783554 | 4/1935 | France | 15/167.2 |
| 2618651 | 2/1989 | France | 15/167.2 |
| 17726 | 8/1898 | Switzerland | 15/167.2 |

*Primary Examiner*—Mark Spisich
*Attorney, Agent, or Firm*—Christopher Duffy

[57] ABSTRACT

The device is a straddle-type device in which the handle thereof has a pair of elongated arms and a cowling on the distal end thereof. The arms extend from the handle in generally parallel relationship to one another, with a slot therebetween, and the cowling is made of plastic resin material and supported on the arms at the distal end portions thereof. The cowling also bridges the slot and has an inverted U-shaped body, which in turn has endmost sections and a midsection therebetween. The endmost sections are encircled about the distal end portions of the arms in intimate contact with the opposing relatively inwardly directed surfaces thereof, as well as the relatively outwardly directed surfaces thereof and the relatively upper, lower and forward peripheral edges thereof. The midsection is flexibly interconnected with and between the endmost sections to form an articulated linkage across the slot, and yieldable bias is built into the arms which tends to pinch the distal end portions of the arms and thus the endmost sections of the cowling together. Meanwhile, fields of bristles that are monolithically upstanding on the relatively inwardly directed surfaces of the endmost sections, form brushes which engage the relatively inside and outside faces of the teeth when the device is straddled about a row of teeth at the cowling, and then translated along the length of the row while the brushes grip the teeth under the bias on the distal end portions of the arms, and the linkage serves to preserve that bias when the diameter of the teeth varies from one tooth to another.

16 Claims, 7 Drawing Sheets

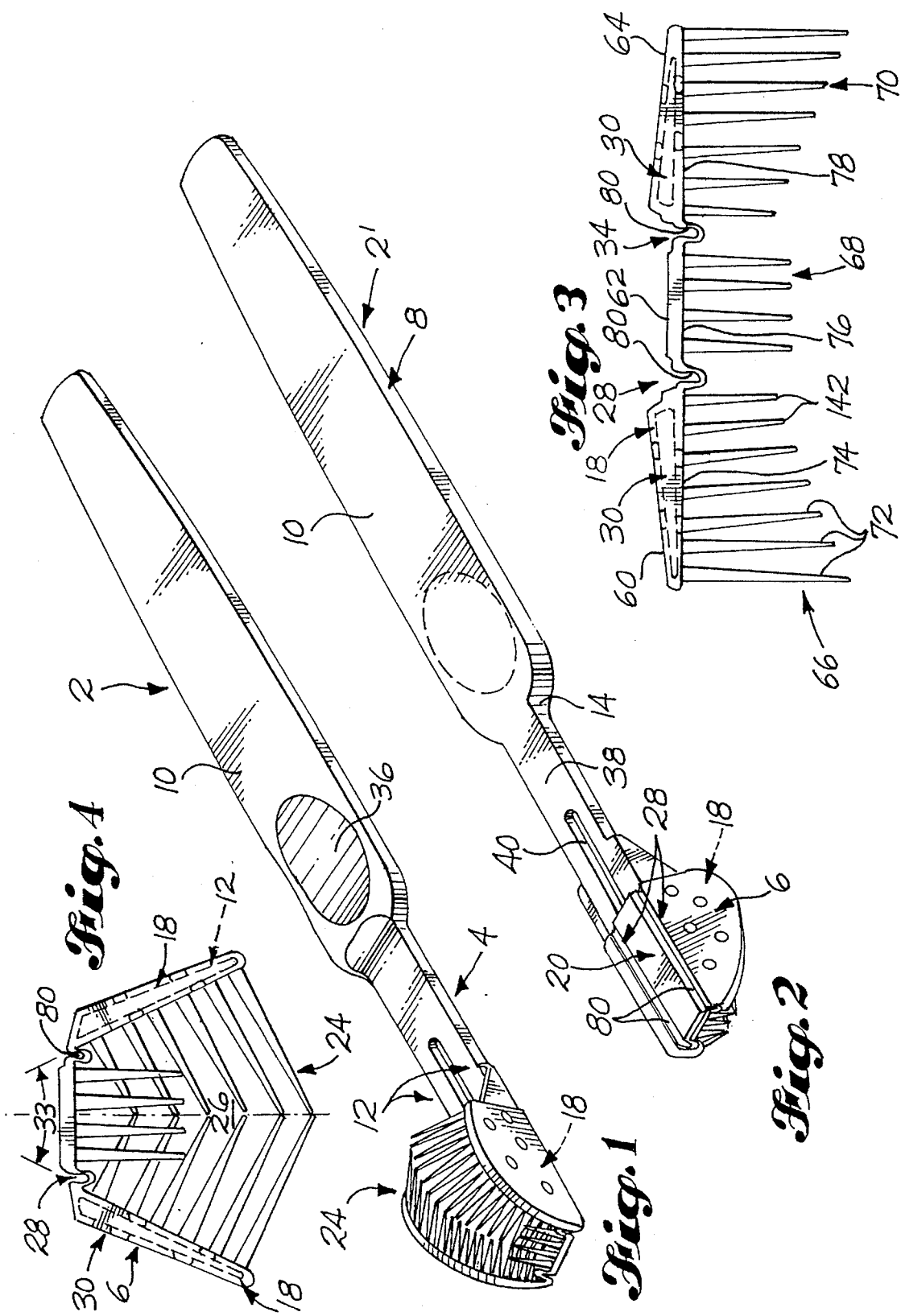

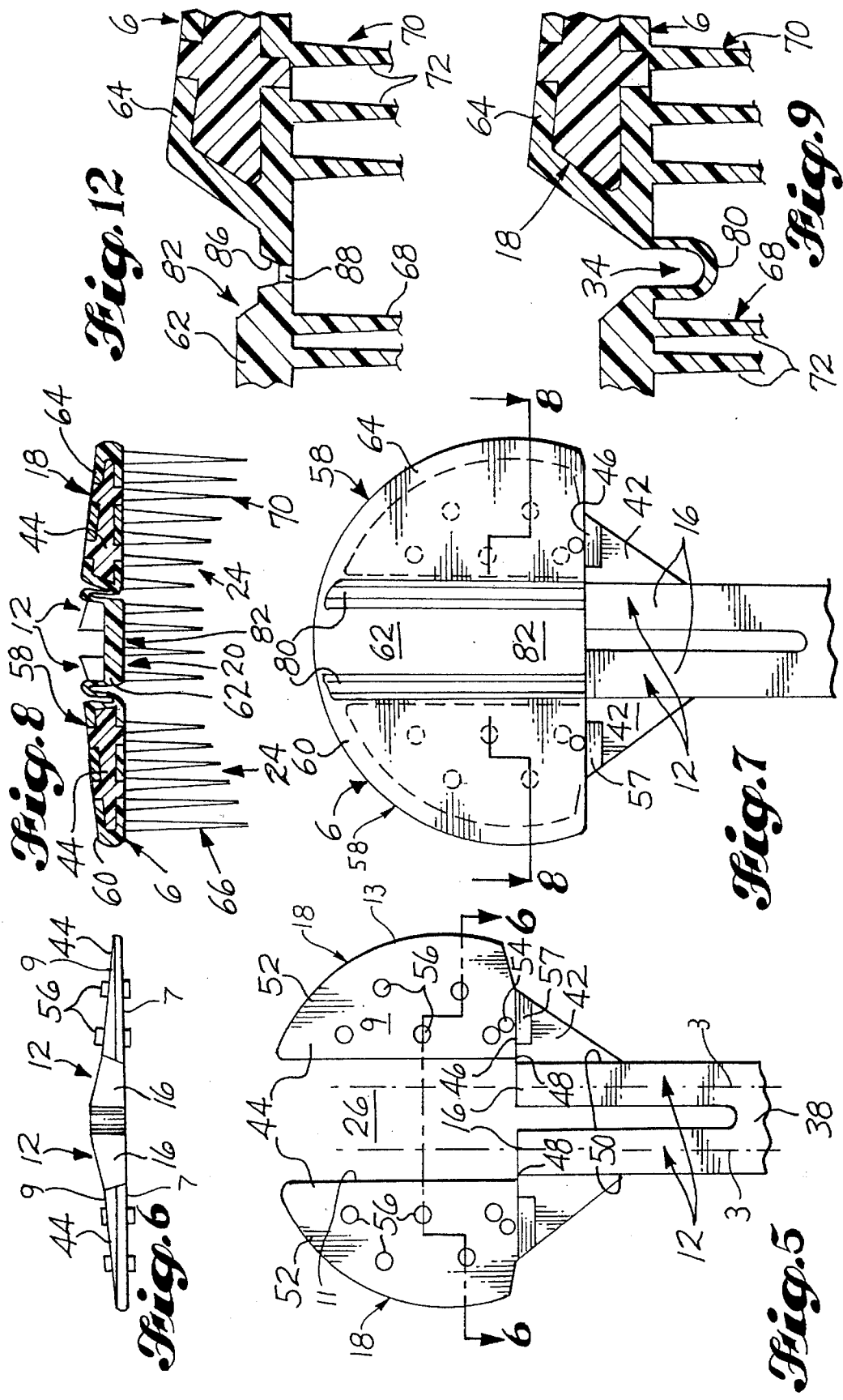

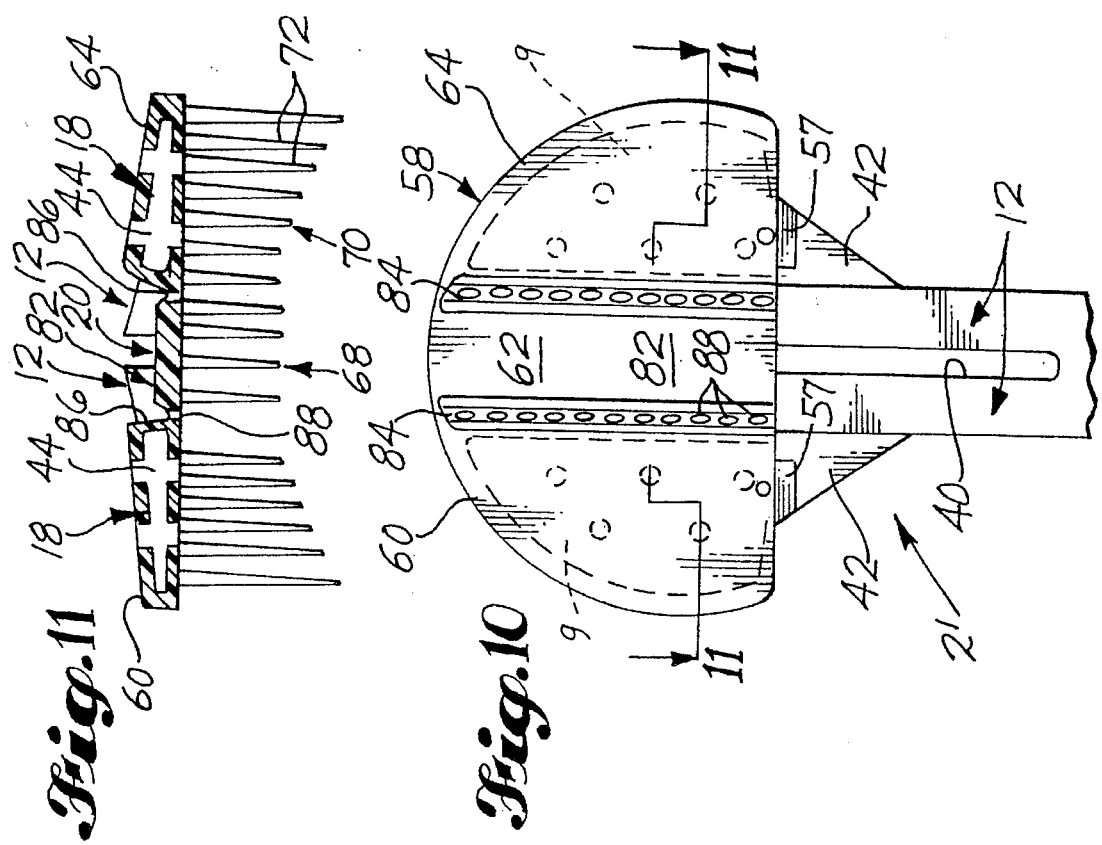

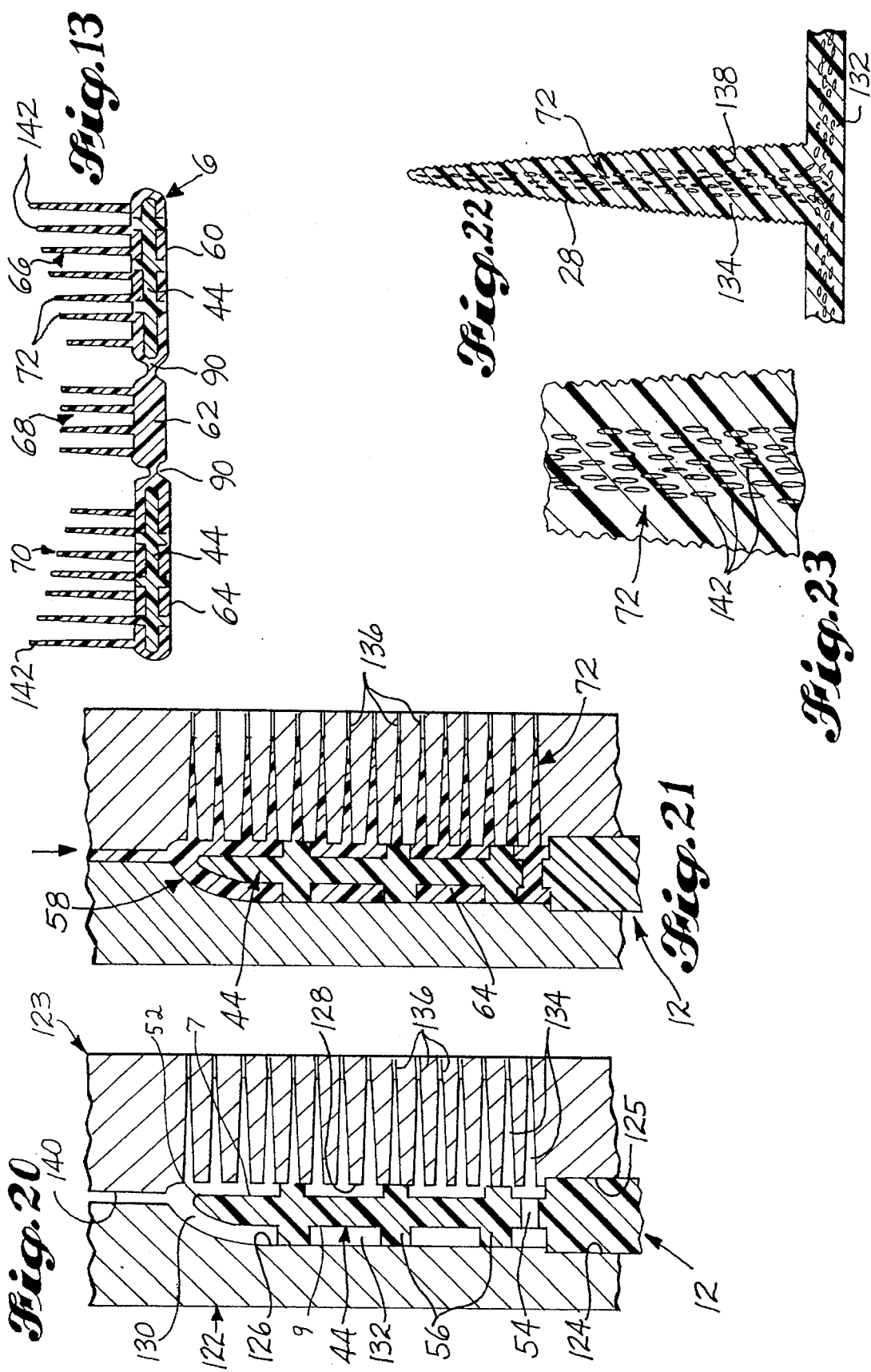

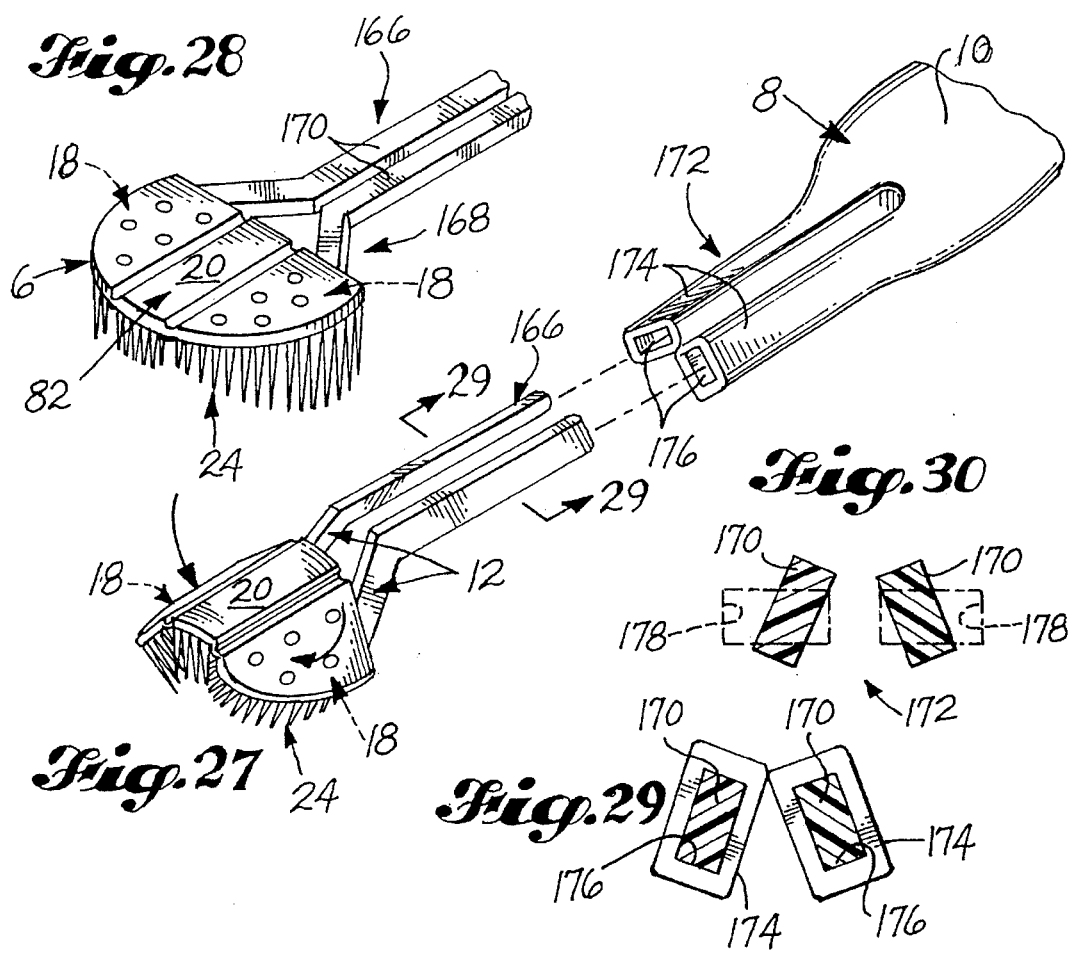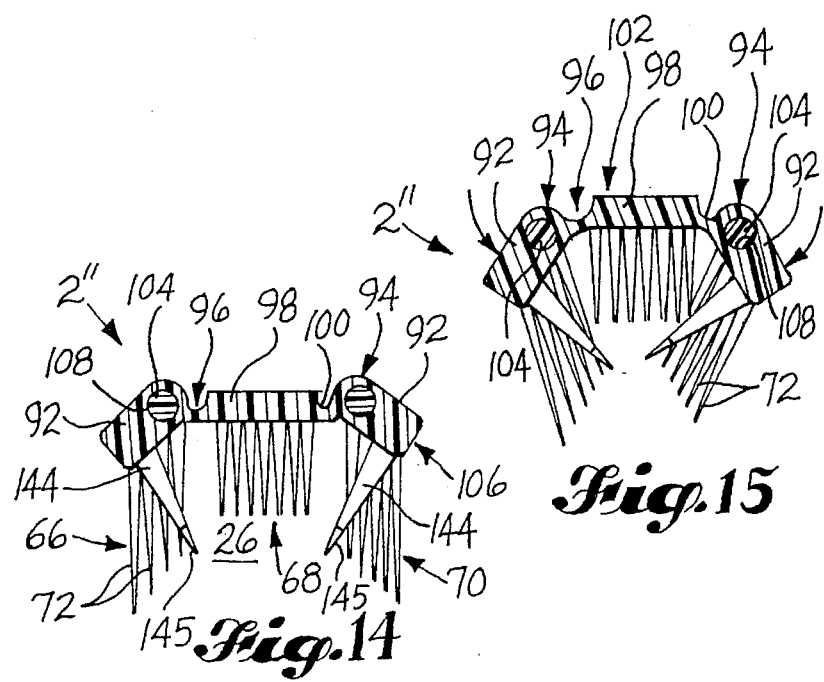

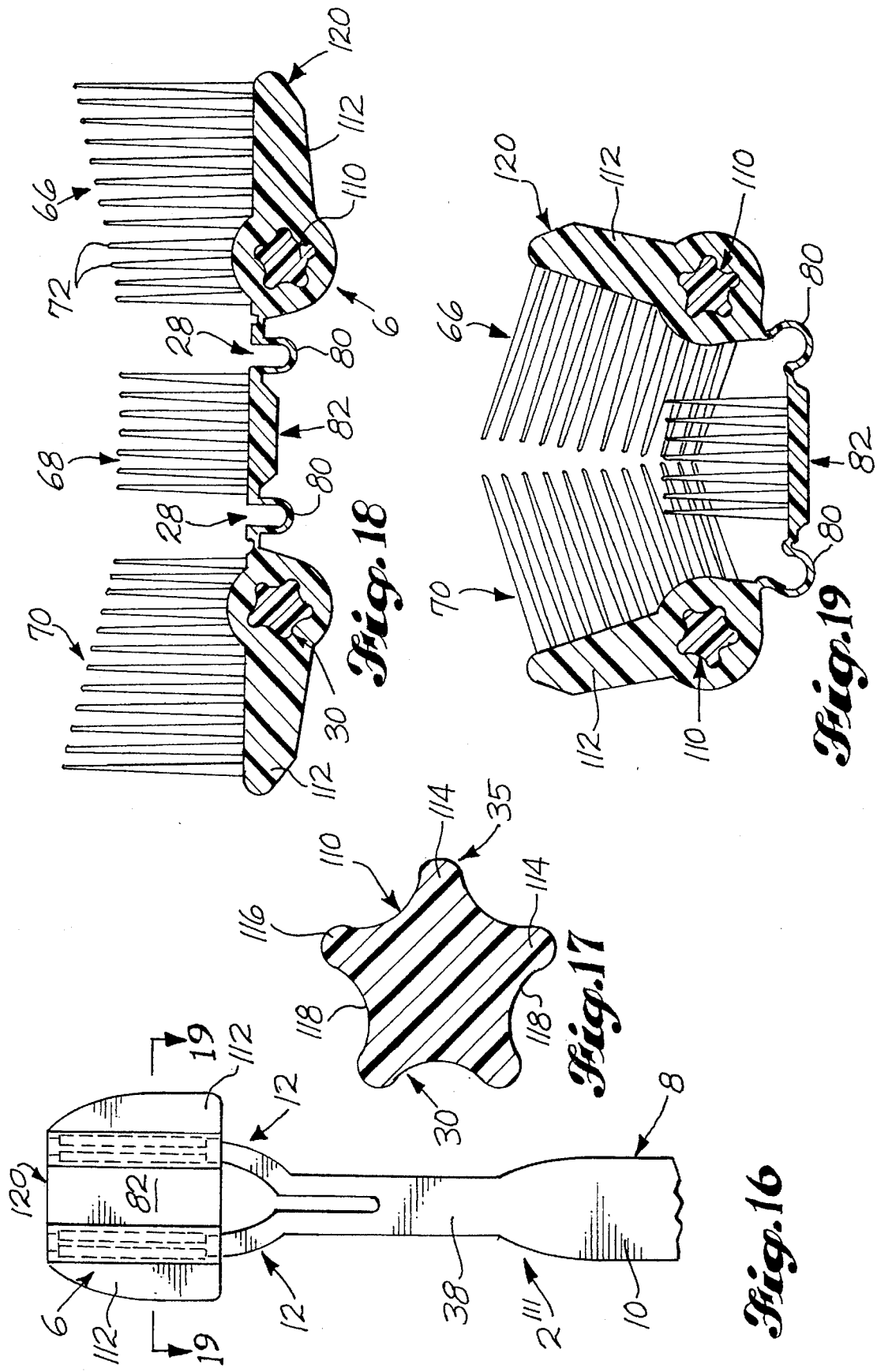

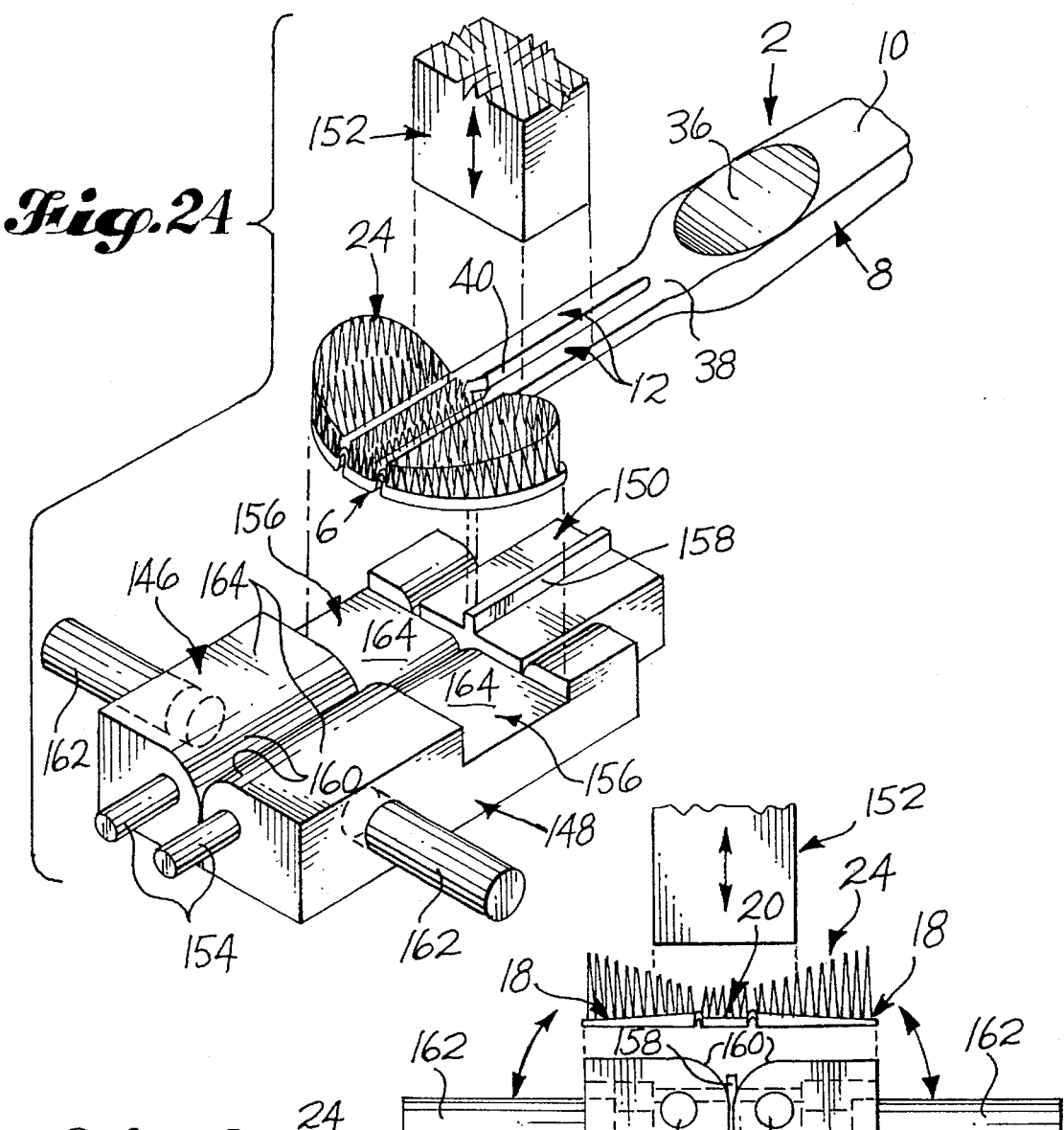
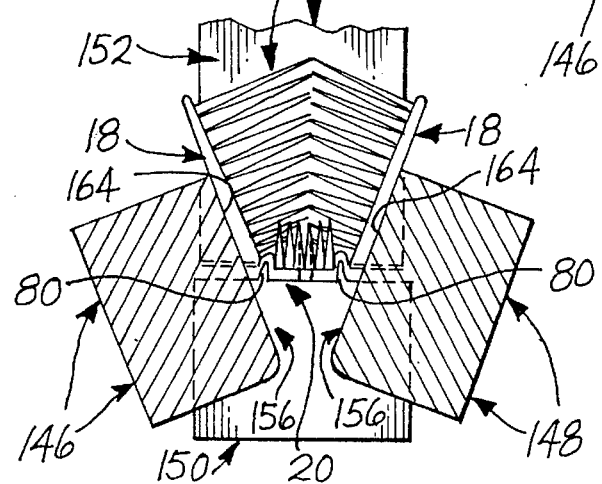

TOOTH BRUSHING DEVICE

RELATED APPLICATIONS

The present Application is a Continuation of application Ser. No. 08/238,144 filed May 4, 1994, now abandoned, which is a Continuation of application Ser. No. 975,013 filed Nov. 12, 1992, under the same title, and now abandoned, which in turn was a Division of application Ser. No. 499,022 filed Mar. 26, 1990 under the same title and now U.S. Pat. No. 5,171,066, application Ser. No. 499,022 was in turn a Continuation in Part of abandoned application Ser. No. 145,771 filed Jan. 19, 1988. Application Ser. No. 145,771 was a Continuation in Part of application Ser. No. 937,554 filed on Dec. 4, 1986 under the title TOOTH BRUSH AND GUM MASSAGER WITH WATER SPRAY and later abandoned. Application Ser. No. 145,771 was then abandoned in favor of application Ser. No. 664,487 filed on Mar. 4, 1991 under the same title. U.S. Pat. No. 5,137,039 issued from application Ser. No. 664,487.

U.S. Pat. No. 137,039 is hereby incorporated into the present Application by this reference to it.

In addition to the forgoing, application Ser. No. 924,096 was filed on Aug. 3, 1992 under the title of application Ser. No. 664,487, as a Continuation thereof, and is now U.S. Pat. No. 5,284,168. Application Ser. No. 926,837 was filed on Aug. 7, 1992 under the title of application Ser. No. 664,487, as a further Continuation thereof, but was abandoned in favor of application Ser. No. 040,078 which was filed on Mar. 30, 1993 under the title of application Ser. No. 926,837, and abandoned in turn in favor of application Ser. No. 185,766 filed Jan. 24, 1994 and now U.S. Pat. No. 5,360,025. Application Ser. No. 978,712 was filed on Nov. 19, 1992 under the title of application Ser. No. 449,022, as a Continuation thereof, and that Application is now U.S. Pat. No. 5,224,764. Application Ser. No. 191,968 was filed Feb. 4, 1994 under the title of application Ser. No. 924,096, as a Continuation thereof, and now U.S. Pat. No. 5,360,026.

A Continuation in Part of application Ser. No. 449,022 was filed on Dec. 11, 1992 under the title APPARATUS AND TECHNIQUE FOR INJECTION MOLDING A PLASTIC MONOLITH, was given Ser. No. 989,125, and now abandoned. A Continuation in Part of both application Ser. No. 664,487 and application Ser. No. 499,022 was filed on Aug. 3, 1992 under the title STRADDLE-TYPE TOOTH BRUSHING DEVICE, and was given Ser. No. 924,099, and is now U.S. Pat. No. 5,316,027. Application Ser. No. 250,049 was filed May 27, 1994, under the title of application Ser. No. 924,099 as a Continuation thereof, and is still pending.

TECHNICAL FIELD

This invention relates to a tooth cleaning device and a method for making the device, and in particular, to a device, and a method for making the same, of the straddle type.

BACKGROUND ART

U.S. Pat. No. 5,137,039 discloses a straddle-type tooth brushing device comprising means including a pair of elongated arms having tooth brushing means on the distal end portions thereof forming a head for straddling about a row of teeth to be cleaned, elongated support means including a handle for supporting the head adjacent the row of teeth, and leveraging means acting on the tooth brushing means from within the head to yieldably bias the tooth brushing means into engagement with the inside and outside faces of the teeth when the head was straddled about the row thereof. The support means had a distal end, and the arms had longitudinal axes and were rigidly interconnected with the support means at the distal end thereof so as to form relatively rigid longitudinal extensions of the support means which projected from the distal end of the support means in generally spaced parallel relationship to one another and had an elongated slot in the space therebetween which was coextensive with the arms and opened to the outside of the device between the distal end of the support means and the distal end portions of the arms in a central plane of the slot extending between the longitudinal axes of the arms generally parallel thereto. The distal end portions of the arms, meanwhile, had pairs of generally laterally inwardly and outwardly directed surfaces thereon, the laterally inwardly directed surfaces of which were relatively opposed to one another across the central plane of the slot, extended in planes generally parallel to the longitudinal axes of the arms, and had relatively upper, lower and forward edges formed about the peripheries thereof, which were interconnected with one another by the laterally outwardly directed surfaces of the distal end portions of the arms at the outsides thereof, and were disposed relatively remote from, and adjacent to the gum lines of the respective row of teeth being brushed, and forwardly of the surfaces, respectively, when in an operational mode of the device, the head was straddled about the row of teeth so that the central plane of the slot was aligned with the row of teeth, the arms were generally parallel to the row, and the laterally inwardly directed surfaces of the distal end portions of the arms were generally opposed to the inside and outside faces of the teeth in the row. The tooth brushing means comprised a monolithic cowling of plastic resin material which had an operatively inverted U-shaped body extending crosswise the plane of the slot and was comprised of a pair of relatively endmost sections that were spaced apart from one another and mounted on the distal end portions of the arms to form brush forming members thereon that opposed one another across the central plane of the slot and were yieldably biased by the leveraging means to engage the faces of the teeth when the head of the device was straddled about the row of teeth in the operational mode of the device; and moreover, a mid-section which was interconnected with and between the endmost sections of the cowling and flexibly interposed in the slot between the relatively upper peripheral edges of the distal end portions of the arms to form an articulated linkage between the brush-forming members which was spaced apart from the distal end of the support means by the openings of the slot to the outside of the device and operable to preserve the bias on the brush forming members when the head adjusted to the varying diameters of the teeth crosswise the central plane of the slot in the operational mode of the device. The brush forming members had oppositely disposed fields of bristles thereon, the bristles of which were formed by strands of the plastic resin material that upstood monolithically on the brush forming members and were so individually spaced apart from one another on the brush forming members as to be individually laterally deflectable in relation to one another, yet collectively operable to form brushes for the faces of the teeth.

In one group of embodiments, the arms were resiliently flexible crosswise the central plane of the slot, and the distal ends of the arms had laterally projecting jaws thereon, which defined the relatively laterally inwardly and outwardly directed surfaces of the distal end portions of the arms and the relatively upper, lower, and forward edges about the peripheries thereof. The jaws were so operatively inclined to the central plane of the slot in the direction relatively upwardly of the plane, that the jaws yieldably biased the brush forming members relatively toward one another transverse the central plane of the slot for engagement with the faces of the teeth. In certain embodiments, moreover, the jaws were so closely spaced apart from one another at the relatively laterally inwardly directed surfaces thereof, and the tooth brushing members so yieldably biased relatively toward one another in the relaxed state of the device, that the user had to forcibly wedge the teeth between the brush forming members when inserting the teeth between the jaws in the operational mode of the device.

DISCLOSURE OF THE INVENTION

According to the present invention, the cowling is now mounted on the distal end portions of the arms so that the endmost sections of the cowling encircle the distal end portions of the arms in intimate contact with the laterally inwardly and outwardly directed surfaces and the relatively upper and lower peripheral edges of the distal end portions of the arms to form the brush forming members in the head of the device. In this way, the head is made more sanitary and more readily cleanable after use. Moreover, in that group of embodiments wherein the arms are resiliently flexible crosswise the central plane of the slot, and the distal ends of the arms have laterally projecting jaws thereon which define the relatively laterally inwardly and outwardly directed surfaces of the distal end portions of the arms and the relatively upper, lower and forward edges about the peripheries thereof, and wherein the jaws are so operatively inclined to the central plane of the slot in the direction relatively upwardly of the plane, that the jaws yieldably bias the brush forming members relatively toward one another transverse the central plane of the slot for engagement with the faces of the teeth, the endmost sections of the cowling commonly also extend about the forward peripheral edges of the jaws and in intimate contact therewith, to encase the jaws in resin material for the maximum effect.

In certain embodiments of the invention, not only is the midsection of the cowling flexibly interconnected with the respective endmost sections of the cowling, but in addition, the respective connections between the midsection and the respective endmost sections of the cowling have reentrantly folded pleats therein extending generally parallel to the central plane of the slot, so that the articulated linkage formed between the brush forming members is more extensible and contractible in the space between the endmost sections of the cowling, relatively crosswise the central plane of the slot.

Additionally, in certain particularly noteworthy embodiments of the invention for manufacturing purposes, the arms have main portions which terminate independently of one another at points relatively remote from the distal end of the support means, and have brackets thereon which cantilever relatively laterally outwardly from the terminal end portions of the main portions and have relatively outboard portions thereof which project relatively outwardly beyond the terminal ends of the main portions in directions relatively away from the distal end of the support means longitudinally thereof, to form distal end portions of the arms, the laterally inwardly and outwardly directed surfaces of which are disposed at acute angles to the central plane of the slot in the direction relatively upwardly of the plane.

As in U.S. Pat. No. 5,137,039, when the cowling is operatively mounted on jaws, the jaws may be so closely spaced apart from one another at the laterally inwardly directed surfaces thereof and the brush forming members so yieldably biased relatively toward one another in the relaxed state of the device, that the user must forcibly wedge the teeth between the brush forming members when inserting the teeth between the jaws in the operational mode of the device.

As in U.S. Pat. No. 5,137,039, moreover, the strands of bristle in the respective fields of the same may be of varying length so that they have oppositely inclined profiles at the tips thereof, relative to the dimensional plane of the cowling at the midsection thereof. And in addition, the cowling may have an additional field of bristle on the midsection thereof, and particularly, at the inner periphery of the cowling.

Furthermore, as in U.S. Pat. No. 5,137,039, the relatively laterally inwardly directed surfaces of the distal end portions of the arms may be disposed at acute angles to the central plane of the slot in the direction relatively upwardly of the plane, and the strands of bristle on the endmost sections of the cowling may be angled to the central plane of the slot in the opposite direction so that the fields of bristle incline apically to the gum lines of the teeth at approximately forty-five degrees when the head is straddled about a row of teeth in the operational mode of the device and the tooth brushing means are yieldably biased into engagement with the faces of the teeth by the leveraging means.

Additionally, not only may the strands of bristle taper inwardly of their respective longitudinal axes in the direction relatively outward from the respective endmost sections of the cowling, as in U.S. Pat. No. 5,137,039, but in addition, the strands of bristle may have longitudinally extending cores of relatively hard material and sheaths of relatively softer material surrounding the same. The strands of bristle may also have textured surfaces on the exteriors thereof, and/or barbs on the tips thereof.

In some embodiments of the invention, the support means and the arms are fabricated as a monolithic frame having the cowling supported on the distal end portions of the arms. In other embodiments, the distal end of the support means has a pair of sockets therein and the arms are forcibly engaged in the sockets to rigidly interconnect the arms with the support means at the distal end thereof.

According to the present invention, the device may be manufactured by positioning the arms in generally spaced parallel relationship to one another in a plane, enclosing the distal end portions of the arms in a pair of mold cavities which are defined by the mutually opposing faces of a pair of relatively reciprocable members on opposing sides of the plane, and have cross sections collectively corresponding to the body of the cowling, with one of the mold cavities defining members also having sets of elongated bristle defining branches therein which extend transverse to the plane of the arms and open into the face of the one member at the cavity therein. Spacer elements are interposed between the distal end portions of the arms and the faces of the members on the opposing sides of the plane to substantially surround the distal end portions of the arms with unoccupied portions of the cavities, and a mass of plastic resin material is injected into the unoccupied portions of the cavities to substantially encircle the distal end portions of the arms with said material. Meanwhile, the gas in the cavities is vented through the branches of the same when the resin mass substantially encircles the distal end portions of the arms and charges into the branches to form a cowling having bristle relatively upstanding on corresponding sides of the endmost sections thereof.

BRIEF DESCRIPTION OF THE DRAWINGS

These features will be better understood by reference to the accompanying drawings wherein several embodiments of the invention are illustrated, including ones employing jaws on the distal ends of the arms; and wherein in addition, the foregoing method of manufacture is also illustrated in the context of forming a jaw equipped device, the jaws of which are initially positioned coplanar with the plane of the arms, and then, after the cowling has been formed about the jaws, the jaws are reentrantly folded about the linkage, relatively away from the plane of the arms, to fold the cowling in turn into a taco shell shaped configuration.

In the drawings:

FIG. 1 is a perspective view of the underside of a jaw equipped device;

FIG. 2 is a perspective view of the device at the top thereof;

FIG. 3 is a front elevational view of the cowling of the device in the initial unfolded condition thereof;

FIG. 4 is a similar view of the cowling after it has been reentrantly folded into a taco shell shaped configuration;

FIG. 5 is part plan view of the arms of the device before the cowling has been mounted about the jaws thereon;

FIG. 6 is a front elevational view of the arms at that time;

FIG. 7 is a part plan view of the arms of the device when the cowling has been mounted about the jaws thereon, but the jaws have not been reentrantly folded as yet to fold the cowling in turn;

FIG. 8 is a cross sectional view of the jaws and cowling along the line 8—8 of FIG. 7;

FIG. 9 is a part cross sectional view along the same line, but enlarged to illustrate the pleated connections between the midsection and the respective endmost sections or wings of the cowling;

FIG. 10 is a part plan view similar to that of FIG. 7, but wherein a differing form of pleat-like connection is employed between the midsection and the respective endmost sections or wings of the cowling;

FIG. 11 is a cross sectional view of the jaws and cowling along the line 11—11 of FIG. 10;

FIG. 12 is an enlarged cross sectional view along that line, illustrating the differing form of pleat-like connection;

FIG. 13 is a cross sectional view similar to those of FIGS. 8 and 11, but illustrating a third form of flexible connection between the midsection and the respective endmost sections or wings of the cowling;

FIG. 14 is a cross sectional view similar to those of 8, 11 and 13, but illustrating still another embodiment wherein in this instance, the endmost sections or wings of the cowling are mounted on the distal end portions of the arms to provide for relative rotation therebetween, there being extensible and contractible toggle joints between the midsection and the respective endmost sections or wings of the cowling;

FIG. 15 is a similar view when the cowling has been reentrantly folded to activate the respective toggle joints between the respective sections;

FIG. 16 is a plan view of a further embodiment wherein the arms and endmost sections or wings of the cowling are interengaged once again for relative rotation, but with detents therebetween whereby the endmost sections or wings of the cowling can be fixed against relative rotation at angular intervals about the arms;

FIG. 17 is a cross sectional view of the distal end portions of the arms in this last embodiment;

FIG. 18 is a cross sectional view of the distal end portions of the arms and cowling when the cowling is in the initial unfolded condition thereof;

FIG. 19 is a cross sectional view of the arms and cowling along the line 19—19 of FIG. 16 when the cowling has been folded into a taco shell shaped configuration;

FIG. 20 is a cross sectional view of a mold for making each of the cowlings in the various embodiments;

FIG. 21 is a similar cross sectional view of the mold when the resin material has been injected therein;

FIG. 22 is an enlarged cross sectional view of one bristle forming branch of the mold cavity, illustrating a technique by which the strands of bristle are given a relatively harder core longitudinally thereof;

FIG. 23 is a partial but still greater enlargement of the branch seen in FIG. 22;

FIG. 24 is a perspective view of an apparatus for reentrantly folding the endmost sections or wings of a cowling about the midsection thereof, to give the cowling a taco shell shaped configuration;

FIG. 25 is a front elevational view of the apparatus when the head of the device is positioned in the same for the folding operation;

FIG. 26 is a part cross sectional view of the apparatus when the wings of the cowling have undergone the folding operation;

FIG. 27 is a top perspective view of an embodiment of the device wherein the distal end of the support means has a pair of sockets therein and the arms are forcibly engaged in the sockets to rigidly interconnect the arms with the support means at the distal end thereof;

FIG. 28 is a top perspective view of the arms when the cowling is in the initial unfolded condition thereof;

FIG. 29 is a cross sectional view of the device along the line 29—29 of FIG. 27; and FIG. 30 is a part cross sectional, part schematic view of the device when it has been modified to accommodate both the unfolded cowling of FIG. 28 and the taco shell shaped one of FIG. 27.

BEST MODE FOR CARRYING OUT THE INVENTION

As indicated, each device 2 has a relatively unfolded preoperative condition and a taco shell shaped operative condition. Like those shown in U.S. Pat. No. 5,137,039, moreover, each comprises means including a pair of elongated arms 12 having tooth brushing means 24 on the distal end portions 18 thereof forming a head 4 for straddling about a row of teeth (not shown) to be cleaned, elongated support means 8 including a handle 10 for supporting the head 4 adjacent a row of teeth, and leveraging means 30 acting on the tooth brushing means 24 from within the head 4 to yieldably bias the tooth brushing means into engagement with the inside and outside faces of the teeth when the head is straddled about the row thereof. The support means have a distal end 38, and the arms 12 have longitudinal axes 3 (FIG. 5), and are rigidly interconnected with the support means at the distal end thereof so as to form relatively rigid longitudinal extensions of the support means which project from the distal end of the support means in generally spaced parallel relationship to one another and have an elongated slot 40 in the space therebetween which is coextensive with the arms and opens to the outside of the device between the distal end 38 of the support means and the distal end portions 18 of the arms in a central plane 5 (FIG. 4) of the slot extending between the longitudinal axes 3 of the arms generally parallel thereto. The distal end portions 18 of the arms have pairs of generally laterally inwardly and outwardly directed surfaces 7 and 9 (FIGS. 5, 6 and 20) thereon, the laterally inwardly directed surfaces 7 of which relatively oppose one another across the central plane 5 of the slot (FIG. 4), extend in planes generally parallel to the longitudinal axes of the arms, and have relatively upper, lower and forward edges 11, 13 and 52, respectively, formed about the peripheries thereof, which are interconnected with one another by the laterally outwardly directed surfaces 9 of the distal end portions of the arms at the outsides thereof, and are disposed relatively remote from and adjacent to the gum lines of the respective row of teeth being brushed, and forwardly of the surfaces 7 and 9, respectively, when in an operational mode of the device, the head is straddled about the row of teeth so that the central plane 5 of the slot is aligned with the row of teeth, the arms 12 are generally parallel to the row, and the laterally inwardly directed surfaces 7 of the distal end portions of the arms are generally opposed to the inside and outside faces of the teeth in the row. The tooth brushing means 24 comprise a monolithic cowling 6 of plastic resin material which has an operatively inverted U-shaped body extending crosswise the plane 5 of the slot and is comprised of a pair of relatively endmost sections 60, 64 that are spaced apart from one another and encircle the distal end portions 18 of the arms in intimate contact with the laterally inwardly and outwardly directed surfaces 7, 9 and the relatively upper and lower peripheral edges 11, 13 of the distal end portions of the arms to form brush forming members 58 thereon that oppose one another across the central plane of the slot and are yieldably biased by the leveraging means 30 to engage the faces of the teeth when the head of the device is straddled about the row of teeth in the operational mode of the device. The tooth brushing means 24 also comprise a midsection 62 which is interconnected with and between the endmost sections 60, 64 of the cowling and flexibly interposed in the slot between the relatively upper peripheral edges 11 of the distal end portions 18 of the arms to form an articulated linkage 20 between the arms 12 and the brush forming members 58 which is spaced apart from the distal end 38 of the support means 8 by the openings of the slot 40 to the outside of the device and operable to preserve the bias on the brush forming members 58 when the head 4 adjusts to the varying diameters of the teeth crosswise the central plane 5 of the slot in the operational mode of the device. The brush forming members 58 have oppositely disposed fields 66, 70 of bristle thereon, the bristles of which are formed by strands 72 of the plastic resin material that upstand monolithically on the brush forming members 58 and are so individually spaced apart from one another on the brush forming members as to be individually laterally deflectable in relation to one another, yet collectively operable to form brushes for the faces of the teeth.

Like the cowlings seen in U.S. Pat. No. 5,137,039, the midsection 62 of each cowling herein is flexibly interconnected with the respective endmost sections 60, 64 of the cowling, but the respective connections 28 between the midsection and the respective endmost sections have adjustment means therein extending generally parallel to the central plane 5 of the slot whereby the linkage 20 is extensible and contractible crosswise the plane of the slot to enable the brush forming members 58 to maintain the angular relationship 33 seen between them in FIG. 4 when the head of the device accommodates to variance in tooth diameter as the device is translated along a row of teeth in the operational mode thereof. This adjustment means can be seen at 34 in the devices 2' of FIGS. 1–13 wherein the endmost sections of the cowling are interlocked against relative rotation about the distal end portions of the arms; and can be seen at 96 in the device 2" of FIGS. 14 and 15 where the endmost sections are interengaged with the distal end portions of the arms for relative rotation about the latter in the operational mode of the device. Or the adjustment means may be seen at 80 in the device 2'" of FIGS. 16–19 where the endmost sections are interengaged with the distal end portions of the arms for relative rotation thereabout, but there are additional means 35 in the connections between the endmost sections and the distal end portions of the arms whereby the endmost sections can be fixed against relative rotation at angular intervals about the distal end portions in the operational mode of the device.

More particularly, the handle 10 of the device shown in FIGS. 1–9 has a lenticular cross section which is progressively more oblate in the direction of the distal end 38 of the support means 8, and there is a thumb shaped swale 36 in the underside of the handle where if desired, the user can place his thumb while he wraps his fingers about the handle to position the head 4 of the device in his mouth. The distal end 38 of the support means takes the form of a boom-like extension of the handle which is reduced in diameter from it at 14, more rectangular in cross section than the handle, and bifurcated at the distal end thereof to form juxtaposed halves that are resiliently flexible and separated from one another by the slot 40 to serve as the main portions 16 of the pair of arms 12. The main portions in turn have a pair of gusset-like brackets 42 thereon which project to the sides of the main portions 16 from the terminal end portions thereof, and which in turn have clapper shaped jaws 44 outriggered thereon at the relatively forwardly oriented edges 46 thereof. In the preoperative condition Of the device, the jaws 44 are coplanar with the brackets 42 and the main portions 16 of the arms, and are cantilevered from the forwardly oriented edges 46 of the brackets at points 48 more widely spaced than the main portions themselves at their outboard edges 50, so that there is a considerable gap 26 between the jaws at the forward end of the device. The jaws are also given a swept-back configuration along the forward edges 52 thereof, and sets of holes 54 and randomly distributed studs 56 are provided in and on the opposing surfaces 7, 9 of the jaws for reasons which will be explained. Additionally, the jaws are relatively thick, and the brackets are relatively thin so that when the device is put to use and the jaws and cowling are bent into a taco shell shaped configuration for that purpose, bending will occur along bend lines of the head that extend generally parallel to the outboard edges 50 of the main portions 16 of the arms and inside of the points 48 at which the jaws are cantilevered from the brackets. Moreover, to promote this effect still further, the bodies of the brackets 42 are ramped up to those of the jaws at the edges 46 of the brackets so that during the bending operation, the jaws are less likely to bend relative to the brackets than are the brackets relative to the arms. The ramps can be seen at 57.

The cowling 6 is once again a casting, but in this instance, the cowling 6 is cast directly on the jaws 44 to provide a hammock-like body of flexible and/or pliable sheet material which is rigidified in part by the jaws, but adapted to be flexed and/or bent with the jaws into a taco shell shaped configuration for use. The thin monolithic sheet-like body of the cowling has in turn three successively flexibly interconnected sections 60, 62 and 64 therein, all of which have sea urchin-like fields 66, 68 and 70 of bristles 72 upstanding on corresponding sides thereof. In the taco shell shaped configuration of the device, the fields 66 and 70 are mutually opposed to one another on the spaced endmost sections or wings 60 and 64 of the cowling, and the field 68 is interposed between them on the bight or midsection 62 of the cowling. Together, the three fields form an interdigitating "thicket" of bristle that thoroughly engages each tooth when the cowling is straddled about a row of teeth in use. See FIG. 4 and compare this with FIGS. 28 and 32 of U.S. Pat. No. 5,137,039. The fields 66, 70 on the wings 60, 64 may also have pick-like bodies (not shown) therewithin, which serve as stylii for tracing the gum lines of the row, as well as picks for removing debris from the same, but these are not shown and reference should be made once again to U.S. Pat. No. 5,137,039 for the details of the same.

In casting the cowling, the three sections 60, 62, 64 of it are cast in a row crosswise of the central planes of the slot 40, and the endmost sections or wings 60, 64 of the cowling are cast around the jaws 44, so as to suspend the midsection 62 in the gap 26 therebetween. The three sections are cast in unison, moreover, and in addition to the midsection 62, webs 80 of thinner sheet material are also cast within the gap 26, to be supported with the midsection, trestle-like, between the respective wings 60, 64. The webs 80 are cast as reentrantly folded pleats of the thinner material, so that in use, the midsection and pleats form an extensible and contractible expansion joint 82 between the pairs of jaws and wings. Such a joint makes it possible for the respective pairs of jaws and wings to maintain a preset angular relationship 33 between the wings while the wings reciprocate in relation to one another to accommodate to variance in tooth diameter. Given arms 12 which are also resiliently flexible along perpendiculars to the plane of the arms at the main portions 16 hereof, the joint 82 also makes it possible for the respective pairs of jaws and wings to be reciprocated in opposite directions, relative to the plane of the arms, should the user wish to generate a vertical component to the cleaning action of the bristle. And in addition, if desired, the joint also makes it possible for the user to scrub each tooth, and the interstices between teeth, with certain of the crisscross action discussed in U.S. Pat. No. 5,137,039.

Referring now to FIGS. 10–12, it will be seen that in lieu of being cast outside the plane of the cowling and reentrantly folded as pleats 80, the webs may be cast in the plane of the cowling as thin hinge lines 84 which have grooves 86 or other relief at one side thereof, and are perforated lengthwise thereof, as seen at 88 in FIG. 10, so as to give them the necessary extensibility and contractibility to perform like pleats, for example, in a children's tooth brush. Or in the alternative, where the cowling is cast from a suitable elastomeric material, the webs may be cast in the plane as thin hinge lines 90 which have relief on both sides thereof, as in FIG. 13, so as to be sufficiently stretchable to perform like pleats for the purposes of the invention.

In each of the devices 2 described thus far, the jaws 44 were substantially parallel to one another at the aforesaid points 48 thereon, the wings 18 were given substantially fixed angular orientations with the jaws, and the flexible connections 28 between the midsection 20 and the wings included pleat-like linkages 34 therein whereby the midsection could reciprocate along perpendiculars to the plane of the arms to enable the wings to maintain the angular relationship 33 therebetween, when the pairs of jaws and wings reciprocated in conjunction with one another, crosswise of the space between the arms, to accommodate to variance in tooth diameter. In the case of the device 2" shown in FIGS. 14 and 15, however, the wings 92 are rotatable about the distal end portions 94, of the arms and the flexible connections 96 between the midsection 98 and the wings 92 include relatively articulated toggle links 100 therein whereby the midsection 98 reciprocates along perpendiculars to the plane of the arms, to rotate the wings 92 about the distal end portions 94 of the arms, and thereby maintain the angular relationship between the wings when the pairs of arms and wings reciprocate as indicated. In short, then, the midsection 98 and linkages 100 are employed as a toggle joint 102, rather than as an expansion joint 82 of the type which was used in the embodiments of FIGS. 1–13.

More particularly, the distal end portions 94 of the arms now have cylindrical bodies 104 which project, spigot-like, from the brackets (not shown) at the aforesaid points 48 thereon, and when the cowling 106 is cast about the distal end portions of the arms, the wings 92 prove to be rotatable on them, due to the fact that the casts form cylindrical sockets 108 about the portions 104. Initially, the cowling assumes the bat-like, drop-wing configuration seen in FIG. 14, but when the device is put to use, the wings 92 are rotated about the portions 104 to the taco shell-shaped configuration of FIG. 15. This has the effect of elevating the midsection 98 to the position of FIG. 15, and in this position, the midsection will cooperate with the two links 100 in rotating the wings in the manner described, assuming that the links 100 have sufficient stiffness to perform as toggle links. That is, given links 100 of this stiffness, when the wings 92 are forced apart by a larger diameter tooth, and the portions 104 reciprocate with them, the toggle joint 102 comprised of the links 100 and the midsection 98, will effectively rotate the wings through sufficient angular deflection to maintain the angle that was established between them when the cowling 106 was bent into the taco shell-shaped configuration of FIG. 15. Conversely, when the wings close about a tooth of narrower diameter, the joint 102 will toggle the wings in the opposite direction to once again maintain the angle therebetween.

It is also possible to provide a joint wherein the wings can be set at variable angles to one another, but when set, will maintain the angle therebetween because of the operation of an expansion joint 82 therebetween. Referring now to the device 2''' shown in FIGS. 16–19, it will be seen that the distal end portions 110 of the arms 12 have axially extending flutes 114 thereon which are symmetrically arrayed about the axes of the portions and rounded at the respective crests 116 and valleys 118 therebetween, so that given a sufficiently deformable material for the cowling 120, and a relatively non-deformable one for the distal end portions of the arms, such as relatively soft and hard plastic materials, respectively, the wings 112 can be rotated about the portions from one flute 114 to the next, and when so rotated, the flutes will serve as detents for preserving the angular relationship between the wings during the use of the device as a toothbrush. When the device is out of use, however, the wings may be reset to some other angle, such as the relatively planar pre-operative condition seen in FIG. 18. Then, when the device is put back into use again, they may be rotated once more to the taco shell-shaped configuration seen in FIG. 19.

Alternatively, the distal end portions 110 of the arms may be polygonal in cross-section, such as pentagonal, to provide detents at the corners of their outlines.

Preferably, in all embodiments, the strands 72 of bristle have a core of relatively harder material at the center thereof, and a sheath of relatively softer material surrounding the same. Also, the arms and support means, are preferably constructed of one material, such as a relatively hard plastic material, and the cowling is constructed of another material which is softer than that of the arms and support means, such as a relatively softer plastic material.

Referring now to FIGS. 20–23, a process is shown for casting a plastic hammock-like cowling 58 around the jaws 44 of the arms 12 (FIGS. 1–13), while at the same time giving the cowling strands 72 of bristle which have relatively harder cores surrounded by the softer plastic material of the cowling itself. According to the process, jaws 44 of relatively high melting temperature plastic resin are clamped between a pair of relatively reciprocable mold cavity-forming members 122, 123, the opposing faces 124, 125 of which have recesses 126, 128 therein that complement one another in forming cavities 130 that correspond to the bodies of the wings 60, 64 when the recesses 126, 128 are registered with one another as shown. When the jaws are so clamped, however, the studs 56 of the jaws abut the members, so that interstitial spaces 132 remain among the studs on each side of the cavities, to allow molten, relatively low melting temperature plastic resin to be introduced around the jaws, on all sides thereof. The cavities 130 are interconnected, meanwhile, by an intermediate cavity (not shown) corresponding in size and shape to the body of the midsection 62 of the cowling, as well as to the bodies of the webs 80 interconnecting it with the wings 60, 64. In addition, at what is to become the inside faces 74, 76, 78 of the wings and midsection, there are conical branches 134 which are recessed into the adjacent member 123 on perpendiculars to the face 125 thereof, and the branches 134 have small outlet ports 136 at the tips thereof for the escape of gas from the cavities 130 of the mold. The branches 134 form the bristle 72 for the tooth brushing means 24 on the corresponding sides of the wings and midsection, and preferably an electric discharge machine is used to form the branches themselves so that the walls 138 of the branches are knurled to provide texture for the bristle formed therein.

Injection ports 140 are provided for the respective cavities 130, as well as the intermediate cavity, and in the process the relatively low melting temperature plastic resin is injected into the cavities to flow about the sets of studs 56 and to fill the cavities with resin, including the holes 54 therebetween. The resin also flows into the branches 134, to charge them as well, and as it does, any gas entrained in the resin escapes through the ports 136 at the tips of the branches. Throughout the operation, moreover, elongated rods 142 of a harder high melting temperature resin are added to the molten resin, to be introduced to the respective branches with the resin, as shown in FIGS. 22 and 23. Because of their length, and because of the fluid mechanics of the flow, the rods 142 tend to orient directionally of the flow, and at the center of the mass thereof in each branch. The rods 142 also remain solid in the molten mass, and agglomerate down the centers of the branches 134, where they closely compact with one another and become elongated stems of harder material at the cores of the bristle formed in the branches.

Commonly, a hard plastic resin with a melting temperature of about 600° F. is used in the jaws 44 themselves, and a softer resin with a melting temperature of about 225° F. is used in forming the cowling 58 about the jaws. Examples of suitable resin materials are given in the earlier Application and include certain polycarbonates, such as General Electric's "LEXAN" brand of polycarbonates, for the frame 4, 8 of each device, and certain thermoplastic elastomers, such as ethyl vinyl acetate, for the cowling 58.

Commonly, the cowling 58 is made up as a planar substrate having the bristle 72 perpendicularly outstanding thereon, and in addition, at varying lengths on the wings 60, 64 thereof, so that the fields 66, 70 have oppositely inclined profiles at the tips 142 thereof, relative to the dimensional plane of the substrate at the midsection 62 thereof. There may also be stylus-like means upstanding in the bristle on the wings, as seen at 144 in FIGS. 14 and 15, and once again, as in U.S. Pat. No. 5,137,039, the stylus-like means may be made semi-rigid to perform as picks. The picks may also have barbs 145 at the ends thereof, to aid in their function as such.

As was also described in U.S. Pat. No. 5,137,039, and is seen in FIG. 14, the substrate may be given a drop wing configuration in which the wings 92 are obliquely angled to the plane of the midsection at, say, 165 degrees to each side thereof.

Substrates such as those made up for the embodiments of FIGS. 14 and 15, and FIGS. 16–19, are commonly positioned in the cavity by sets of retractable pins (not shown), inserted for example, between the branches 134 of the member 123 on that side of the cavity, and through the member 122 on the other side thereof.

The substrate may be reentrantly folded into a generally U-shaped configuration using, for example, the device illustrated in FIGS. 24–26. The device comprises a pair of rotary platens 146 and 148, and a pair of clamps 150 and 152 with which to secure the tooth brushing device 2 in position on the platens while the platens are rotated in relation to one another to reentrantly fold the jaws 18 and wings 60, 64 of the device about the midsection 20, as seen in FIG. 26. The platens 146, 148 are rotatably mounted on a pair of spaced parallel shafts 154, and they have adjoining saddles 156 recessed therein, crosswise of the shafts, to receive the head 4 of the tooth brushing device as shown. The lower clamp 150, meanwhile, is stationary and has a keyway 158 upstanding along the center thereof, in line with the vertical plane dividing the pair of platens. The keyway 158 is adapted to insert within the slot 40 between the arms 12 of the tooth brushing device, and the upper clamp 152 is reciprocably mounted to be lowered into clamping engagement with the arms 12 when they are straddled about the keyway 158 to rest the head 4 on the pair of saddles 156 of the platens. In addition, the platens 146,148 are rounded at the adjacent corners 160 thereof, so that they can be rotated inward of one another in the manner seen in FIG. 26, using a pair of handles 162 that project from the outsides thereof. As the platens are rotated, the upper sides 164 of the saddles 156 abut the wings 60, 64 of the substrate, as well as the brackets 42 of the arms 12, and bend the same into an angle 33 adapted to provide the gap needed between the wings for use of the device as a straddle-type tooth brush.

Alternatively, head 4 may be bent into the desired U-shaped configuration by the technique seen in FIGS. 27–30. The head 4 is manufactured as a separate assembly 168 in which there is a pair of prongs 170 having the arms 12 as extensions thereof, as seen in FIG. 28. Meanwhile, the handle 10 of the support means 8, has a bifurcated extension 172, the two portions 174 of which provide sockets 176 for the prongs 170 of the head assembly. The sockets 176 are rectangular in cross section and angled toward one another at the same angle 33 as that needed between the wings 18 of the assembly. When the prongs 170 are rotated to that angle, to give the assembly the U-shaped configuration seen in FIG. 27, the prongs 170 may then be bayoneted into the sockets 176 of the extension 172 to render the device ready for use, the prongs, meanwhile, forcibly engaging in the sockets 176 to tightly secure the assembly to the support means 8 at the required angle.

In still another version, the extension 172 of the handle is equipped with two pairs of sockets 176, 178, one of which, 178, is coplanar to receive the pronged ends 170 of the assembly 168 when it is in the unfolded condition thereof, and the other pair of which, 170, is angularly related to receive the pronged ends of the assembly when it is bent into the U-shaped condition thereof. Such a version is especially suited to the marketing of the brush in the most compact form, i.e., the condition of FIG. 28, whereafter the assembly 168 is removed from the sockets 178, bent into the taco shell-shaped condition, and then reinserted in the sockets 170 to render it useful as a straddle-type device.

I claim:

1. A straddle type tooth brushing device comprising:

means including a pair of elongated arms having toothbrushing means on distal end portions thereof forming a head for straddling about a row of teeth to be cleaned, elongated support means including a handle for supporting the head adjacent the row of teeth, and leveraging means acting on the tooth brushing means from within the head to yieldably bias the tooth-brushing means into engagement with the inside and outside faces of the teeth when the head is straddled about the row thereof, said support means having a distal end, said arms having longitudinal axes and being rigidly interconnected with the support means at, the distal end of the support means so as to form relatively rigid longitudinal extensions of the support means which project from the distal end of the support means in generally spaced parallel relationship to one another and have an elongated slot in the space therebetween which is coextensive with the arms and opens to the outside of the device between the distal end of the support means and the distal end portions of the arms in a central plane of the slot extending between the longitudinal axes of the arms generally parallel thereto, the distal end portions of the arms having pairs of generally laterally inwardly and outwardly directed surfaces thereon, the laterally inwardly directed surfaces of which are relatively opposed to one another across the central plane of the slot, extend in planes generally parallel to the longitudinal axes of the arms, and have relatively upper, lower and forward edges formed about the peripheries thereof, which are interconnected with one another by the laterally outwardly directed surfaces of the distal end portions of the arms at the outsides thereof, and are disposed relatively remote from, and adjacent to the gum lines of the respective row of teeth being brushed, and forwardly of the surfaces, respectively, when in an operational mode of the device, the head is straddled about the row of teeth so that the central plane of the slot is aligned with the row of teeth, the arms are generally parallel to the row, and the laterally inwardly directed surfaces of the distal end portions of the arms are generally opposed to the inside and outside faces of the teeth in the row, the tooth brushing means comprising a monolithic cowling of plastic resin material which has an operatively inverted U-shaped body extending crosswise the plane of the slot and is comprised of a pair of relatively endmost sections that are spaced apart from one another and each encircle the distal end portion of a respective one of the arms in intimate contact with the laterally inwardly and outwardly directed surfaces and the relatively upper and lower peripheral edges of the distal end portions of the arms to form brush-forming members thereon that oppose one another across the central plane of the slot and are yieldably biased by the leveraging means to engage the faces of the teeth when the head of the device is straddled about the row of teeth in the operational mode of the device, and a mid-section which is interconnected with and between the endmost sections of the cowling and flexibly interposed in the slot between the relatively upper peripheral edges of the distal end portions of the arms to form an articulated linkage between the brush-forming members which is spaced apart from the distal end of the support means by the openings of the slot to the outside of the device and operable to preserve the bias on the brush forming members when the head adjusts to the varying diameters of the teeth crosswise the central plane of the slot in the operational mode of the device, the brush-forming members having oppositely disposed fields of bristles thereon, the bristles of which are formed by strands of the plastic resin material that upstand monolithically on the brush forming members and are so individually spaced apart from one another on the brush forming members as to be individually laterally deflectable in relation to one another, yet collectively operable to form brushes for the faces of the teeth.

2. The straddle-type tooth brushing device according to claim 1, wherein the arms are resiliently flexible crosswise the central plane of the slot, and the distal ends of the arms have laterally projecting jaws thereon which define the relatively laterally inwardly and outwardly directed surfaces of the distal end portions of the arms and the relatively upper, lower and forward edges about the peripheries thereof, and wherein the jaws are so operatively inclined to the central plane of the slot in the direction relatively upwardly of the plane, that the jaws yieldably bias the brush forming members relatively toward one another transverse the central plane of the slot for engagement with the faces of the teeth.

3. The straddle-type tooth brushing device according to claim 2, wherein the endmost sections of the cowling also extend about the forward peripheral edges of the jaws and in intimate contact therewith, to encase the jaws in resin material.

4. The straddle-type tooth brushing device according to claim 2 wherein the jaws are so closely spaced apart from one another at the relatively laterally inwardly directed surfaces thereof, and the brush forming members so yieldably biased relatively toward one another in the relaxed state of the device, that the user must forcibly wedge the teeth between the jaws in the operational mode of the device.

5. The straddle-type tooth brushing device according to claim 1 wherein the arms have main portions which terminate independently of one another at points relatively remote from the distal end of the support means, and have brackets thereon which cantilever relatively laterally outwardly from the terminal end portions of the main portions and have relatively outboard portions thereof which project relatively outwardly beyond the terminal ends of the main portions in directions relatively away from the distal end of the support means longitudinally thereof, to form distal end portions of the arms, the relatively laterally inwardly directed surfaces of which are disposed at acute angles to the central plane of the slot in the direction relatively upwardly of the plane.

6. The straddle-type tooth brushing device according to claim 1 wherein the strands of bristle in the respective fields of the same are of varying length so that they have oppositely inclined profiles at the tips thereof.

7. The straddle-type tooth brushing device according to claim 1 wherein the cowling also has an additional field of bristle on the midsection thereof.

8. The straddle-type tooth brushing device according to claim 7 wherein the additional field of bristle is disposed relatively inside of the operatively inverted U-shaped body of the cowling.

9. The straddle-type tooth brushing device according to claim 1 wherein the relatively laterally inwardly directed surfaces of the distal end portions of the arms are disposed at acute angles to the central plane of the slot in the direction relatively upwardly of the plane, and the strands of bristle on the endmost sections of the cowling are angled to the central plane of the slot in the opposite direction so that the fields of bristle incline apically to the gum lines of the teeth at approximately 45 degrees when the head is straddled about a row of teeth in the operational mode of the device and the tooth brushing means are yieldably biased into engagement with the faces of the teeth by the leveraging means.

10. The straddle-type tooth brushing device according to claim 1 wherein the support means and the arms are fabricated as a monolithic frame having the cowling supported on the distal end portions of the arms.

11. The straddle-type tooth brushing device according to claim 1 wherein the distal end of the support means has a pair of sockets therein and the arms are each forcibly engaged in a respective one of the sockets to rigidly interconnect the arms with the support means at the distal end thereof.

12. The straddle-type tooth brushing device according to claim 1 wherein the strands of bristle have longitudinally extending cores of relatively hard material and sheaths of relatively softer material surrounding the same.

13. The straddle-type tooth brushing device according to claim 1 wherein the strands of bristle have bodies which taper inwardly of their respective longitudinal axes, in the direction relatively outward from the respective endmost sections of the cowling.

14. The straddle-type tooth brushing device according to claim 1 wherein the strands of bristle have textured surfaces on the exteriors thereof.

15. The straddle-type tooth brushing device according to claim 1 wherein the strands of bristle have barbs on the tips thereof.

16. The straddle-type tooth brushing device according to claim 1 wherein the respective connections between the midsection and the endmost sections have reentrantly folded pleats therein which extend generally parallel to the central plane of the slot and render the respective connections flexible.

* * * * *